United States Patent [19]

Trummlitz et al.

[11] 4,328,235

[45] May 4, 1982

[54] SUPPRESSING PAIN WITH BENZOTHIAZOL-2(3H)-ONES

[75] Inventors: Günter Trummlitz, Warthausen; Wolfhard Engel, Biberach; Günther Schmidt, Biberach; Wolfgang Eberlein, Biberach; Ernst Seeger, Biberach; Günther Engelhardt, Biberach; Rainer Zimmermann, Mittelbiberach, all of Fed. Rep. of Germany

[73] Assignee: Boehringer Ingelheim GmbH, Ingelheim am Rhein, Fed. Rep. of Germany

[21] Appl. No.: 163,965

[22] Filed: Jun. 30, 1980

[30] Foreign Application Priority Data

Jul. 6, 1979 [DE] Fed. Rep. of Germany ....... 2927352

[51] Int. Cl.³ ......................................... A61K 31/425
[52] U.S. Cl. ..................................................... 424/270
[58] Field of Search ......................................... 424/270

[56] References Cited

PUBLICATIONS

Hunter et al., J. Chem. Soc., (1935), p. 1755.

*Primary Examiner*—Stanley J. Friedman
*Attorney, Agent, or Firm*—Hammond & Littell, Weissenberger and Muserlian

[57] ABSTRACT

There are described pharmaceutical compositions containing as active substances benzothiazol-2(3H)-ones of the general formula

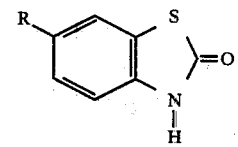

wherein R represents a hydrogen atom or a methyl, methoxy, or ethoxy group. The pharmaceutical compositions serve as analgesics and antipyretics and possess little or no methemoglobin-forming activity.

5 Claims, No Drawings

SUPPRESSING PAIN WITH BENZOTHIAZOL-2(3H)-ONES

This invention relates to pharmaceutical compositions containing benzothiazol compounds. More particularly, this invention relates to pharmaceutical compositions containing benzothiazol-2(3H)-ones of the general formula

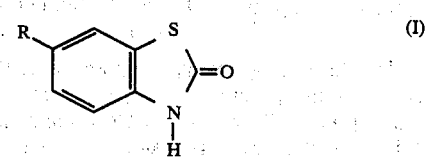

wherein R represents a hydrogen atom or a methyl, methoxy, or ethoxy group.

Compounds corresponding to those of Formula I are known. In a technical chemical paper, R. F. Hunter and E. R. Parken described the compounds 6-methyl- and 6-ethoxy-benzothiazol-2(3H)-one (J. Chem. Soc., 1935, page 1755). Furthermore, the compound benzothiazol-2(3H)-one has also been discussed (J. Chem. Soc., 1930, page 125). With regard to the latter compound, the literature indicates an antimicrobial and fungistatic acitivity [W. Nimmich, Pharmazie, 19, (4), 281 (1964)].

The 6-methoxy-benzothiazol-2(3H)-one is described in the publication Friedländer, 22/1, page 324 (1939) [see, also, Chem. Abstr., 29, 6250 (1935)]; however, nothing has been stated with regard to pharmacological activity. In the literature benzothiazoles analogous to Formula I are often mentioned as intermediates for the preparation of dyestuffs and pharmaceuticals.

Therefore, it was quite surprising to find that the compounds of Formula I exhibit a very good analgesic activity as well as a distinct antipyretic activity and that the compounds are pharmacologically acceptable. In addition, in contrast to analgesics with similar activity such as, for example, phenacetin, the compounds of Formula I show either a significantly diminished me-themoglobin-forming activity or none at all.

The compounds of general Formula I can be prepared in the following manner:

A 2-amino-thiophenol of general formula

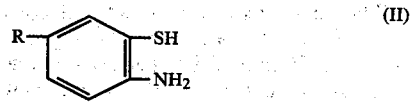

wherein R is as defined above, is reacted with N,N'-carbonyl diimidazole in an anhydrous solvent such as benzene, toluene, or another hydrocarbon or in tetrahydrofurane, dioxane, or a similar cyclic ether at temperatures up to the boiling point of the reaction mixture. For the further processing, that is, to recover the compounds of Formula I, it is generally sufficient to remove the solvent in vacuo and to recrystallize the reaction product from, for example, 1,2-dichloroethane, ethanol, or methanol.

The 2-amino-thiophenols of Formula II used as starting products are known from the literature, and they can be prepared according to known methods. Thus, for example, 2-amino-thiophenol (b.p.: 80°–81° C./3 mbar, m.p.: 92°) is obtained by the heating of 2-mercapto-benzothiazole with sodium hydroxide solution under pressure [see, G. G. Skvortsova, Z. V. Stepanova, and S. M. Tyrina, Zh. Organ. Khim., 2 (9), 1656 (1966)]. The compounds 2-amino-5-methyl-thiophenol (m.p.: 90° C.), 2-amino-5-methoxy-thiophenol (m.p.: 104° C.), and 2-amino-5-ethoxy-thiophenol (m.p.: 104° C.) are obtained by hydrolysis of the corresponding 2-amino-benzothiazole with boiling aqueous potassium hydroxide solution [see, R. L. Mital and S. K. Jain, J. Chem. Soc. (C), 1969, 2148, or S. K. Jain and R. L. Mital, Z. Naturforsch., 32 B, 821 (1977)].

As already mentioned above, the compounds of general Formula I possess a very good analgesic and antipyretic activity with either slight or no methemoglobin-forming activity. To demonstrate these characteristics, the compounds A = 6-Ethoxy-benzothiazol-2(3H)-one,
B = 6-Methoxy-benzothiazol-2(3H)-one, and
C = 6-Methyl-benzothiazol-2(3H)-one were tested in comparison with
D = Phenacetin with regard to analgesic activity in the mouse and in the rat, antipyretic activity in the rat, and methemoglobin-forming activity in the cat, as well with regard to acute toxicity in the mouse.

Activity against the Sensitivity of the Mouse in the Hot Plate Test

The test was performed according to the method described by CHEN and BECKMAN [Science, 113, 631 (1951)] in male Chbb:NMRI (SPF)-mice with an average weight of 20 grams. The "hot plate" consisted of aluminium and had a temperature of 52° C. on its surface.

The test substances were administered as trituration in 1% methyl cellulose (0.1 ml/10 g of mouse) by means of an oesophageal tube.

Before treatment with the test substances, the animals were twice put on the hot plate at an interval of 30 minutes, whereby their individual times of reaction were measured. After treatment with a test substance, the times of reaction of the animals were again measured in an interval of 30 minutes.

From the average maximum increase of the time of reaction obtained after treatment with different doses, and after linear regression analysis according to LINDER [Statistische Methoden, 4th ed., pp. 148–162, Birkhäuser, Basel 1964], an $ED_{100}$ dose with the confidence limits according to FIELLER [Quart. Journal Pharmacol., 17, 177–123 (1944)] was calculated. The $ED_{100}$ dose is one which increased the time of reaction by 100%. The results of the testing are set forth in the following table:

TABLE 1

| Test Compound | $n_1$* | $n_2$** | $ED_{100}$ (mg/kg) | Confidence Limits at 95% Probability (mg/kg) |
|---|---|---|---|---|
| A | 3 | 10–20 | 154.1 | (83.4–208.3) |
| B | 3 | 10 | 122.0 | (58.9–154.4) |
| C | 3 | 10 | 143.9 | (78.0–197.2) |
| D | 5 | 10 | 327.7 | (208.9–431.8) |

*Number of tested doses
**Number of animals/dose

Activity against the Pain of Inflammation on the Back Paw of the Rat

The activity against the pain caused by inflammation was tested according to the method of RANDALL-SELITTO [Arch. Int. Pharmacodyn., 111, 409 (1957)] in male Chbb:THOM-rats, which had body weights of 100 to 130 grams. The test compounds were administered 135 minutes after induction of the yeast oedema as a trituration in 1% methyl cellulose by means of an oesophageal tube. After a further 45 minutes the pain threshold was determined in the animals treated with the test compound and in the control animals treated only with the vehicle. By using linear regression analysis according to LINDER, an $ED_{50}$ was calculated with the confidence limits according to FIELLER, the $ED_{50}$ being the dose which increased the pain threshold by 50%. The results of this testing were as follows:

TABLE 2

| Test Compound | $n_1$ | $n_2$ | $ED_{50}$ (mg/kg) | Confidence Limits at 95% Probability (mg/kg) |
|---|---|---|---|---|
| A | 3 | 10 | 64.3 | (56.8–74.5) |
| B | 3 | 10 | 142.2 | (129.6–158.5) |
| C | 3 | 10 | 54.4 | (50.3–59.0) |
| D | 3 | 10 | 273.8 | (250.0–304.2) |

Antipyretic Activity

The temperture-lowering activity was tested by the observation of the temperature curve given by rectally measured body temperatures of partially immobilized Chbb:THOM-rats having body weights between 125 and 150 grams. The test substances were administered as a trituration in a 1% methyl cellulose in portions of 1.0 ml/100 g of animal using an oesophageal tube.

From the values for the average maximum decline of temperature, which were gained after the administration of the different doses of the test substances, and after a linear regression analysis according to LINDER, an $ED_{-1.5°\,C.}$ was calculated with the confidence limits according to FIELLER as the dose which decreases the body temperature by 1.5° C. The results of the testing are set forth in the following table:

TABLE 3

| Test Compound | $n_1$ | $n_2$ | $ED_{-1.5°\,C.}$ (mg/kg) | Confidence Limits at 95% Probability (mg/kg) |
|---|---|---|---|---|
| A | 3 | 11–12 | 84.3 | (73.4–95.4) |
| B | 4 | 8–12 | 66.8 | (57.1–78.4) |
| C | 3 | 9 | 30.9 | (23.9–36.9) |
| D | 4 | 9–11 | 34.4 | (28.5–41.7) |

Determination of the Level of Methemoglobin in the Cat

The test substances were administered to cats of both sexes having an average body weight of 2.5 kg, as a trituration in 1% methyl cellulose using an oesophageal tube (2 ml/kg; the oesophageal tube was cleared in situ by aqua bidestillata). After a single application blood-tests were taken by heart-punctuation at different times, that is, at 3 hours, 5 hours, 24 hours, and 48 hours after administration. The photometric registration of the spectrum of hemoglobin as well as the determination of the content of hemoglobin in comparison to controls were effected according to the method of LEMBERG and LEGGE [Hematin Compounds and Bile Pigments, Interscience Publishers, New York (1949)]. The results of the testing were as follows:

TABLE 4

| Test Compound[4] | Dose (mg/kg) | 3 hours after Administration | | | 5 hours after Administration | | | 24 hours after Administration | | | 48 hours after Administration | | |
|---|---|---|---|---|---|---|---|---|---|---|---|---|---|
| | | $n^1$ | $\bar{x}^2$ | $SD^3$ | n | $\bar{x}$ | SD | n | $\bar{x}$ | SD | n | $\bar{x}$ | SD |
| A | 50 | 3 | 0.3 | 0.4 | 3 | 0.5 | 0.4 | 3 | 1.1 | 1.3 | | | |
| | 100 | 5 | 0.4 | 0.5 | 5 | 0.1 | 2.2 | 5 | 0.3 | 0.8 | | | |
| | 200 | 5 | 1.0 | 1.7 | 5 | 0.4 | 0.6 | 5 | 0.5 | 1.0 | | | |
| B | 100 | 5 | 4.6 | 4.2 | 5 | 3.5 | 5.0 | 4 | 0.0 | 0.1 | | | |
| | 200 | 5 | 8.1 | 6.6 | 5 | 11.7 | 5.9 | 5 | 0.0 | 0.2 | | | |
| C | 100 | 4 | 4.0 | 6.1 | 4 | 2.4 | 4.2 | 4 | 0.1 | 0.4 | | | |
| | 200 | 7 | 13.6 | 10.6 | 7 | 13.7 | 8.7 | 7 | 0.4 | 0.9 | | | |
| D | 25 | 4 | 1.9 | 2.1 | 4 | 0.4 | 0.3 | — | | | | | |
| | 50 | 7 | 19.6 | 9.6 | 7 | 9.8 | 6.7 | 7 | 0.5 | 0.8 | | | |
| | 100 | 12 | 32.0 | 17.7 | 10 | 35.8 | 17.2 | 12 | 0.5 | 0.6 | | | |
| | 200 | 10 | 36.0 | 17.2 | 10 | 46.6 | 16.4 | 13 | 15.4 | 22.1 | 9 | 1.1 | 1.5 |

[1]Number of animals
[2]Average value of methemoglobin (% of total hemoglobin)
[3]Standard deviation (% of total hemoglobin)
[4]Control values for methemoglobin level before treatment: n = 54, $\bar{x}$ = 0.03%, SD = 0.9%

Acute Toxicity in Mice

The acute toxicity was determined in Chbb-NMRI (SPF)-mice of both sexes, having an average body weight of 20 grams. The test compounds were administered as a trituration in 1% methyl cellulose (0.5 ml/10 g of animal) by means of an oesophageal tube. The calculation of the $LD_{50}$ values was effected according to the method of LITCHFIELD and WILCOXON [J. Pharmacol. Exp. Ther., 96. 99 (1949)], based on the percentage of animals which died within 14 days after administration of different doses. The results of the testing are set forth in the following table:

TABLE 5

| Test Compound | $n_1$ | $n_2$ | $LD_{50}$ (mg/kg) | Confidential Limit at 95% Probability (mg/kg) |
|---|---|---|---|---|
| A | 3 | 10–20 | 1200 | (984–1464) |
| B | 3 | 10 | 1280 | (1130–1450) |
| C | 3 | 10 | 2160 | (1460–3200) |
| D | 3 | 10–20 | 1459 | (1231–1709) |

The compounds A to C showed, with regard to the sensitivity in the hot plate test, after oral administration, an activity which is two times higher than that of the known phenacetin, that is, compound D (see, Table 1). Also, in the rat the analgesic activity of the compounds A to C was two to five times higher than that of the phenacetin (see, Table 2).

As can be seen from Table 3, the compounds A to C showed, like phenacetin, an antipyretic activity, in addition to the analgesic activity. While the acute toxicity of the compounds A to C largely corresponds to the acute toxicity of the phenacetin (see, Table 5), it can be seen from Table 4 that compounds A to C have either no methemoglobin activity or that such activity is lower with regard to compounds A to C than with regard to phenacetin, compound D.

The compounds of general Formula I can be incorporated into conventional pharmaceutical preparations, such as tablets, coated tablets, suppositories, capsules, or juices. The single dose for adults contains from about 20 to 600 mg (from about 0.3 to 9 mg/kg), preferably from about 50 to 300 mg (from about 0.7 to 4.5 mg/kg), of active ingredient and the daily dose contains from about 60 to 1800 mg (from about 0.9 to 26 mg/kg), preferably from about 180 to 900 mg (from about 2.6 to 13 mg/kg), of active ingredient.

The following examples are intended to illustrate the invention and are not to be construed as limiting the invention thereto.

EXAMPLES

Example 1

6-Ethoxy-benzothiazol-2(3H)-one

An amount of 1.69 g (0.01 mol) of 2-amino-5-ethoxy-thiophenole and 1.78 g (0.011 mol) of N,N'-carbonyl diimidazole was stirred for two hours in 100 ml of anhydrous benzene. After refluxing for one hour, the reaction mixture was filtered. The solvent was evaporated from the filtrate at a diminished pressure, and the remaining residue was recrystallized from 1,2-dichloroethane. Eight hundred and twenty milligrams (42% of theory) of 6-ethoxy-benzothiazol-2(3H)-one were obtained.

M.p.: 147° C.

$C_9H_9NO_2S$ (195.24): Calc.: C 55.37, H 4.65, N 7.17, S 16.42: Found: C 55.30, H 4.54, N 7.05, S 16.12.

Example 2

Benzothiazol-2(3H)-one

The above compound was prepared by means of a procedure analogous to that of Example 1 from 2-amino-thiophenole and N,N'-carbonyl diimidazole in tetrahydrofurane.

Yield: 79% of theory,

M.p.: 136°–137° C. (methanol)

$C_7H_5NOS$ (151.19): Calc.: C 55.61, H 3.33, N 9.27, S 21.21: Found: C 55.60, H 3.48, N 9.26, S 21.00.

Example 3

6-Methyl-benzothiazol-2(3H)-one

In accordance with a procedure analogous to that of Example 1, the above compound was prepared from 2-amino-5-methyl-thiophenole and N,N'-carbonyl diimidazole.

Yield: 50% of theory,

M.p.: 169°–170° C. (ethanol).

$C_8H_7NOS$ (165.22): Calc.: C 58.16, H 4.27, N 8.48, S 19.40: Found: C 58.25, H 4.20, N 8.62, S 19.55.

Example 4

6-Methoxy-benzothiazol-2(3H)-one

The above compound was prepared from 2-amino-5-methoxy-thiophenole and N,N'-carbonyl diimidazole using a procedure analogous to that of Example 1.

Yield: 47% of theory,

M.p.: 163.5°–164° C. (1,2-dichloroethane).

$C_8H_7NO_2S$ (181.22): Calc.: C 53.02, H 3.89, N 7.73, S 17.69: Found: C 53.25, H 3.90, N 7.65, S 17.65.

Example 5

Tablets containing 50 mg of 6-Ethoxy-benzothiazol-2(3H)-one

| Component | Amount (mg) |
|---|---|
| Active ingredient | 50.0 |
| Lactose | 128.0 |
| Potato starch | 40.0 |
| Magnesium stearate | 2.0 |
| | 220.0 |

Method of preparation

A 10% mucus was prepared from the potato starch by heating. The active ingredient, the lactose, and the remaining potato starch were mixed, and together with the mucus prepared the mixture was granulated through a screen of mesh size 1.5 mm. The granulate was dried at 45° C., granulated again through the above mentioned screen, mixed with magnesium stearate, and pressed into tablets.

Weight of tablets: 220 mg

Punch: 9 mm.

Example 6

Coated Tablets containing 50 mg of 6-Ethoxy-benzothiazol-2(3H)-one

The tablets prepared according to Example 5 were covered with a coating in conventional manner, which coating consisted essentially of sugar and talcum. The finished coated tablets were polished by means of bees wax.

Weight of coated tablets: 300 mg.

Example 7

Capsules containing 60 mg of 6-Ethoxy-benzothiazol-2(3H)-one

One capsule contains 60.0 mg of active ingredient.

Method of preparation

The active ingredient was micronized and filled into capsules, which capsules were subsequently closed.

Example 8

Suppositories containing 60 mg of 6-Ethoxy-benzothiazol-2(3H)-one

Composition of one suppository:

| Component | Amount (mg) |
|---|---|
| Active ingredient | 60.0 |
| Suppository mass (e.g., cocoa butter or Witepsol W 45 ®, available from Fa. Chemische Werke | |

-continued

| Component | Amount (mg) |
|---|---|
| Witten GmbH) | 1640.0 |
| | 1700.0 |

Method of preparation

Finely powdered active ingredient was suspended in melted suppository mass, which suspension was cooled to 40° C. The mass was poured at 37° C. into slightly pre-cooled suppository forms.
Weight of suppositories: 1.70 g Example 9

Tablets containing 200 mg of 6-Ethoxy-benzothiazol-2(3H)-one

Composition of one tablet:

| Component | Amount (mg) |
|---|---|
| Acetylsalicylic acid | 250.0 |
| Active ingredient | 200.0 |
| Caffein | 50.0 |
| Corn starch, direct compressible | 50.0 |
| Lactose, direct compressible | 90.0 |
| Stearin talcum (2 + 8 trituration) | 10.0 |
| | 650.0 |

Method of preparation

The components were mixed to form a homogeneous mass and pressed into tablets.
Weight of tablets: 650 mg
φ: 13 mm, biplanar, bilateral facet and unilateral notch.

Example 10

Tablets containing 200 mg of 6-Ethoxy-benzothiazol-2(3H)-one

Composition of one tablet:

| Component | Amount (mg) |
|---|---|
| Active ingredient | 200.0 |
| Lactose | 120.0 |
| Corn starch | 70.0 |
| Polyvinyl pyrrolidone | 8.0 |
| Magnesium stearate | 2.0 |
| | 400.0 |

Method of preparation

The active ingredient, the lactose, and the corn starch were moistened homogeneously in an aqueous solution of polyvinyl pyrrolidone, granulated through a screen of mesh size 2.0 mm, and dried at 50° C. in a circulation air drier. After a second granulation, through a screen of mesh size 1.5 mm, magnesium stearate was added, and the mixture was pressed into tablets.
Weight of tablets: 400 mg
φ: 11 mm, round, biplanar, bilateral facet and unilateral notch.

Example 11

Tablets containing 200 mg of 6-Ethoxy-benzothiazol-2(3H)-one

Composition of one tablet:

| Component | Amount (mg) |
|---|---|
| Active ingredient | 200.0 |
| Codeine phosphate | 15.0 |
| Lactose | 110.0 |
| Corn starch | 65.0 |
| Polyvinyl pyrrolidone | 8.0 |
| Magnesium stearate | 2.0 |
| | 400.0 |

Method of preparation

The active ingredient, the codeine, phosphate, the lactose, and the corn starch were moistened with an aqueous solution of polyvinyl pyrrolidone, granulated through a screen of mesh size 2.0 mm, and dried at 50° C. in a circulation air drier. After a second granulation, through a screen of mesh size 1.5 mm, magnesium stearate was added, and the mixture was pressed into tablets.
Weight of tablets: 400 mg
φ: 11 mm, round, biplanar, bilateral facet and unilateral notch.

Example 12

Suppositories containing 200 mg of 6-Ethoxy-benzothiazol-2(3H)-one

Composition of one suppository:

| Component | Amount (mg) |
|---|---|
| Active ingredient | 200 |
| Hard fat (e.g., Witepsol H 19 ® or Witepsol W 45 ®, available from Fa. Chemische Werke Witten GmbH) | 1500 |
| | 1700 |

Method of preparation

The hard fat was melted. At 38° C. the pulverized active ingredient was homogeneously dispersed in the melt. The mass was cooled to 35° C. and poured into slightly pre-cooled suppository forms.
Weight of suppositories: 1.70 g.

Example 13

Suspension containing 200 mg of 6-Ethoxy-benzothiazol-2(3H)-one

Composition of 100 ml of suspension:

| Component | Amount |
|---|---|
| Active ingredient | 4.0 g |
| Carboxymethyl cellulose | 0.1 g |
| Methyl p-hydroxybenzoate | 0.05 g |
| Propyl p-hydroxybenzoate | 0.01 g |
| Cane sugar | 10.0 g |
| Glycerin | 5.0 g |
| Sorbite solution 70% | 20.0 g |
| Flavoring agent | 0.3 g |
| Distilled water | to 100.0 ml |

Method of preparation

Distilled water was heated up to 70° C. Under stirring the methyl p-hydroxybenzoate and the propyl p-hydroxybenzoate, as well as the glycerin and carboxymethyl cellulose, were dissolved therein and then the solution was cooled to room temperature. The active ingredient was added under stirring and homogeneously dispersed. After adding and dissolving the sugar, the sorbite solution, and the flavoring agent, the suspension was evacuated in vacuo under stirring. Five milliliters of suspension contained 200 mg of active ingredient.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method of suppressing pain in a host which comprises administering to a host in need of such treatment an effective amount of analgesic pharmaceutical composition consisting essentially of an inert pharmaceutical carrier and as active ingredient a benzothiazol-2(3H)-one of the formula

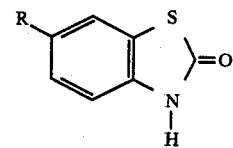

wherein R represents a hydrogen atom or a methyl, methoxy, or ethoxy group.

2. The method of claim 1, wherein R represents a methyl, methoxy, or ethoxy group.

3. The method of claim 2, wherein R is an ethoxy group.

4. The method of claim 2, wherein R is a methoxy group.

5. The method of claim 2, wherein R is a methyl group.

* * * * *

UNITED STATES PATENT AND TRADEMARK OFFICE
CERTIFICATE OF CORRECTION

PATENT NO. : 4,328,235
DATED : May 4, 1982
INVENTOR(S) : GÜNTER TRUMMLITZ ET AL.

It is certified that error appears in the above—identified patent and that said Letters Patent is hereby corrected as shown below:

Column 2, line 53: "177-123" should read -- 117-123 --.
Column 5, line 39: "dichloroe-" should read
-- dichloro- --.
       line 40: "thane" should read -- ethane --.

Column 6, in line 16, please insert
-- Composition of one tablet: --

Signed and Sealed this

Seventeenth Day of August 1982

[SEAL]

Attest:

GERALD J. MOSSINGHOFF

Attesting Officer    Commissioner of Patents and Trademarks